United States Patent
Raith et al.

[11] Patent Number: 5,994,497
[45] Date of Patent: Nov. 30, 1999

[54] COMPOSITIONS HAVING A PHOSPHAZENE DERIVATIVE AND A CROSS-LINKING AGENT

[75] Inventors: Thomas Raith, Wernau; Wolfgang Nuding, Ulm, both of Germany

[73] Assignee: DaimlerChrysler AG, Stuttgart, Germany

[21] Appl. No.: 08/964,409

[22] Filed: Nov. 4, 1997

[30] Foreign Application Priority Data

Nov. 4, 1996 [DE] Germany ............................ 196 45 340

[51] Int. Cl.[6] .................................................. C08G 79/02
[52] U.S. Cl. ......................... 528/399; 528/398; 525/255; 525/330.9
[58] Field of Search ..................... 528/399, 398; 525/255, 330.9

[56] References Cited

FOREIGN PATENT DOCUMENTS

| | | |
|---|---|---|
| 0 368 165 | 5/1990 | European Pat. Off. . |
| 0 557 943 | 9/1993 | European Pat. Off. . |
| 1-124616 | 5/1989 | Japan . |
| 6-236770 | 8/1994 | Japan . |

OTHER PUBLICATIONS

Chem Abstract 117:9964 "Curable phosphazene compositions and photochromic products" Akihiko et al JP 90–130396 900522.

113: 154438 "Phosphazene compound compositions for curable coatings" Atounori JP 88–283059 881109.

113: 98757 Phosphazene compositions as antioxidants for magnetic powders Atsinori JP 88–197172 880809.

111: 196099 "Cyclic polyphosphazene group containing crosslinked acrylic plastics for lenses" Masahiro et al JP 87–230951 870917.

111:196098 Polymerizable phosphazene compound compositions for lenses Masahiro et al JP 87–230950 870917.

120:136251 "Antistatic agents" Masahiro JP 92–35902 920224.

112:57762 "Heat curable cyclophosphazene resin compositions for printed circuit hand" Toshio et al. JP 87–292092 871120.

105:227909 "Polymeric composition containing epoxy oligomer and a curing agent" Nickolaev et al SU 84–3753741 840613.

*Primary Examiner*—Duc Truong
*Attorney, Agent, or Firm*—Evenson, McKeown, Edwards & Lenahan, PLLC

[57] ABSTRACT

The invention relates to hardenable compositions which contain as the essential constituent, in the non-hardened condition, at least one phosphazene derivative of the general formula $[NP-(X-Y-Z)_2]_n$, and at least one cross-linking agent with at least two functional groups which are selected among the Z radicals and which can react with the functional Z radicals of the phosphazene derivative is provided, wherein X radicals are from the group —O—, —S—, —NH— or —NR—, preferably oxygen, Y are aliphatic, cycloaliphatic, aromatic and/or heteroaromatic hydrocarbon groups, Z are functional radicals from the group —OH, —NH$_2$, —NCO, —COOH, —CHO, —CH=CH$_2$, allyl, N-methylol, acrylate, methacrylate, silyl, glycidyl or epoxy or preliminary stages of the radicals from this group or radicals from this group which are blocked by protective groups, preferably acrylate or methacylrate radicals and n is an integer of at least 3 and no more than 10;

The NP radicals of the above formula are preferably combined to a phosphazene ring, n being 3 or 4. The phophazene derivatives can be used for the production of hardenable lacquers, coating agents or fillers, knifing fillers, adhesives, preforms or foils.

34 Claims, No Drawings

COMPOSITIONS HAVING A PHOSPHAZENE DERIVATIVE AND A CROSS-LINKING AGENT

BACKGROUND AND SUMMARY OF THE INVENTION

This application claims the priority of German application number 196 45 340.2, the disclosure of which is expressly incorporated by reference herein.

Known hardenable phosphazene compounds have at least one ethylenically unsaturated side group, which can be radically or ionically polymerized. Examples of ethylene derivatives most frequently used as a polymerizable side group are acrylic, methacrylic, vinyl, allyl or styrol radicals.

European Patent Document EP-A-0 557 943 describes phosphazene compounds which can be hardened by radical polymerization and have at least one ethylenically unsaturated, polymerizable side group whose polymerization is initiated by the addition of initiators or by electron beams. European Patent Document EP-A-0 368 165 describes hardenable resin compositions which contain a hardenable phosphazene compound with at least one ethylenically unsaturated, polymerizable side group and, as additional essential constituents, a pentaerythritolacrylate compound and/or a bis-(4-acryloxydialkoxyphenyl) alkane compound. The polymerization of these resin compositions takes place by heating or ultraviolet radiation or electron beams.

As essential constituents of hardenable compositions, the known radically polymerizable phosphazene compounds have a number of disadvantages. For example, they tend to prematurely polymerize so that stabilizers have to be added to the compositions and high temperatures must be avoided. This, in turn, results in disadvantages with respect to the storage life and the selection of the synthesis conditions. During the synthesis, mild reaction conditions must be selected which reduce the yield since, frequently, under these reaction conditions, complete substitution of chlorine on the initial phosphazene cannot be achieved on the initial phosphazene by the side groups.

As a rule, the synthesized phosphazene derivatives are, therefore, not free of chlorine, which is also undesirable. The polymerization reaction of the known phosphazene derivatives, which as a rule takes place radically, is inhibited by atmospheric oxygen. Large initiator radicals must be used in order to achieve an acceptable hardening of the lacquer surface. In particular, the thermal hardening will frequently result in incompletely hardened surfaces. In the case of the hardening of radically polymerizing phosphazene resins, a considerable shrinkage will frequently occur, which results in an impairment of the adhesion and crack formation. For this reason, such phosphazene derivatives or mixtures thereof are unsuitable for many applications, for example, as lacquers, flat coats, or coating agents. To avoid shrinkage, large quantities of low-shrinkage additions are frequently used, which, however, may have other disadvantageous effects on the material characteristics of the hardened end product. European Patent Document EP-A-0 557 943, for example, describes the use of methacrylate derivatives or halogenated polyesters as shrinkage-reducing additions. Pure phosphazene resins, as described, for example, in European Patent Document EP-A-0 368 165, frequently have the disadvantage that their hardening takes place very slowly. If radically polymerizable phosphazene derivatives are used in lacquers or coating agents, the presence of radicals often results in discolorations, which frequently may not occur before the coatings age.

It is one object of the present invention to provide new hardenable compositions, which avoid the indicated disadvantages of the state of the art and furnish hardened products with improved characteristics. In particular, the invention provides a method to avoid a radical reaction mechanism during the harding of the compositions as well as compositions made from this method.

This object is achieved by means of hardenable compositions, which in the non-hardened condition, comprise as the essential constituent at least one phosphazene derivative of the general formula $[NP—(X—Y—Z)_2]_n$, wherein each X is the same or different radical and is selected from the group —O—, —S—, NH— or —NR— (where $R=C_1-C_6$-alkyl);

each Y is the same or different aliphatic, cycloaliphatic, aromatic and/or heteroaromatic hydrocarbon groups, which may optionally contain O, S and/or N;

each Z is the same or different functional radical from the group —OH, —NH$_2$, —NCO, —COOH, —CHO, —CH=CH$_2$, allyl, N-methylol, acrylate, methacrylate, silyl, glycidyl or epoxy or preliminary stages of the radicals from this group or radicals from this group which are blocked by protective groups, in which case no more than four Z radicals may also be —H; and n is an integer of at least 3 and no more than 10;

and at least one cross-linking agent is provided, which has at least two functional groups selected among the Z radicals, which functional groups can react with the functional Z radicals of the phosphazene derivative.

DETAILED DESCRIPTION OF SPECIFIC EMBODIMENTS

The hardening of the compositions according to the invention takes place by polycondensation reactions or polyaddition reactions of the reactive side groups of the phosphazene derivative with those of the cross-linking agent or by way of a mixed reaction mechanism, which in addition to the above-mentioned reaction path, also comprises a radical reaction path. Since neither the phophazene derivative nor the cross-linking agent exclusively carry radically polymerizable side groups, such a reaction, which is connected with the above-described disadvantages, will not occur. It is important that the functional radicals of the phophazene derivative, on the one hand, and of the cross-linking agent on the other hand, are selected such that they react with one another and supply at least one condensation product or addition product. It is also expedient to use different phosphazene derivatives with the same or different functional radicals. If phosphazene derivatives are used with different reactive radicals, these may be selected such that they can react exclusively with the radicals of the other phosphazene derivatives, exclusively with the reactive radicals of a cross-linking agent or with both. The same applies to the cross-linking agent used. Here also, different cross-linking agents can be used with the same or different reactive radicals, which corresponding to the above, may react exclusively with phosphazene derivatives, exclusively with other cross-linking agents or with both. Therefore, because of the multiple variation possibilities, the product characteristics can be arbitrarily influenced corresponding to the requirements.

It is also expedient to use as Z radicals preliminary stages of functional groups or functional groups blocked by protective groups, if there is the danger that the functional groups will prematurely and/or completely react in an undesirable manner as early as during the synthesis of the corresponding compounds or during the mixing with other compounds. ε-caprolactam, butanonoxime and malonic acid diethylester, for example, are particularly suitable as protective groups for isocyanate radicals. Examples of preliminary stages of functional Z radicals are nitrate radicals as the preliminary stage of amino groups or allyl radicals for epoxy groups. Hydroxy groups required for the polymerization of silyl groups can be protected, for example, from the actual condensation reaction by acetyl or amino radicals. The separation of the protective groups can take place by hydrolysis according to the following diagram.

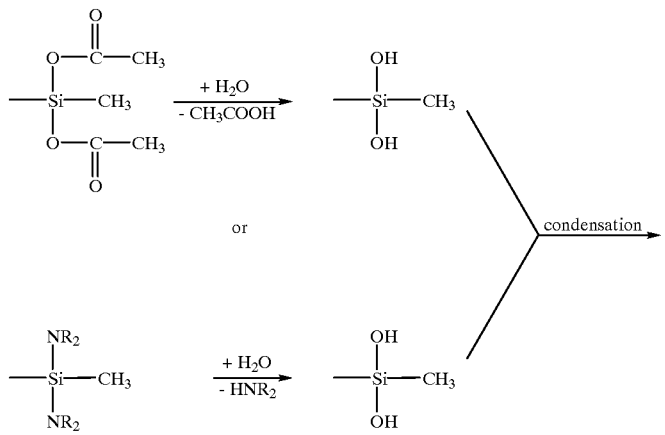

A preferred embodiment of the invention is characterized in that the NP radical of the above formula are combined to a phosphazene ring with alternating N- and P-atoms and n is 3 or 4, particularly preferably 3. In the case of particularly suitable phosphazene derivatives, the X quantity is oxygen and/or the Y radical of the above formula is linear or branched $C_1$–$C_{10}$-alkylene, $C_1$–$C_{10}$-oxyalkylene, $C_1$–$C_{10}$-alkylene phenyl, $C_1$–$C_{10}$-alkylene carboxyphenyl, phenylene, biphenylene, alkaoxyphenylene or oxyphenylene.

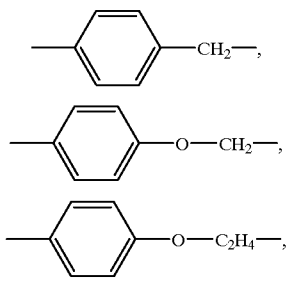

1,4-phenylene, $C_1$–$C_{10}$-alkylphenylene or $C_1$–$C_{10}$-alkylcarboxylphenylene were found to be particularly suitable Y radicals.

In a specific embodiment of the invention, n is equal to 3 and 2; 3 or 4 of the Z radicals are acrylate or methacrylate radicals. Compounds are therefore obtained which can advantageously be polymerized in a multi-step process, specifically by way of a radical reaction mechanism of the acrylate or methacrylate radical, on the one hand, and a polycondensation or polyaddition of the remaining radicals, on the other hand.

The phosphazene derivatives according to the invention can be produced with high yields with full substitution of the phosphazene and can therefore be free of chlorine. The hardening of the phosphazene derivative according to the invention is not inhibited by oxygen and even thin coats are completely hardened in the presence of atmospheric oxygen, which, in particular, permits the thermally or ionically initiated hardening. The hardening of the compositions according to the invention expediently takes place after the application to a substrate. They have no tendency or at least a reduced tendency to discolor the hardened products, which makes them suitable, among others, particularly also for clear or light lacquers, coats, fillers, thin coats and adhesives, in the case of which, in additional to the functional characteristics, the visual characteristics are also important.

An advantage of the compositions according to the invention is also their low tendency to shrink. Lacquers and other surface coats, which contain hardenable compositions of the present invention as the essential constituent, exhibit very good adhesive characteristics and form no cracks.

All these characteristics make the hardenable compositions according to the invention suitable for a use as binding agents or hardening agents for lacquers, coating agents, fillers, knifing fillers, adhesives, preforms or foils. Their use is particularly advantageous in transparent coatings for the exterior paint coat or for the paint coat on mounted wooden parts in vehicles, in transparent coatings for diffused-light lenses for headlights made of polycarbonate, and the like.

Conventional additives, such as initiators, pigments, spreading expedients, dyes, UV-stabilizers, fillers, and the like can also be added to the hardenable compositions of the present invention.

In the non-hardened condition of the compositions, the structure of the phosphazene derivatives may be ring-shaped or chain-shaped but in every case has a basic structure with alternating nitrogen and phosphorous atoms. However, the ring compounds with 3 or 4 NP quantities are preferred, the 6-ring with 3 N atoms and 3 P atoms being particularly preferred.

The phosphazene derivatives according to the invention can be produced by reacting chlorophosphazene with a compound of the general formula M—(—X—Y—Z), wherein X, Y and Z are as defined above; that is, Z is a functional radical or a precursor of a reactive radical or a radical provided with a protective group, and M is a hydrogen atom, an alkali metal, an alkaline earth metal or a base radical. The base quantity M may, for example, be a pyridyl radical or a tertiary amino quantity, such as a triethylamino radical, or the 1,8-diazabicyclo-(5,4,0)-undec-7-en(1,5-5) radical. M being sodium is preferred. The compounds M—(—X—Y—Z) can be obtained by the reaction of the H—(—X—Y—Z) compounds with sodium hydride, sodium metal, sodium hydroxide or sodium carbonate, as, for example, according to the process of U.S. Pat. No. 4,775,732. Methoxy, benzyl, aldehyde, amino, allyl, 3,4-dihydro-2H-pyranyl-(DHP), nitro or ethyl ester radicals, for example, are suitable for a use as preliminary stages or as radicals of functional groups Z provided with protective groups. The reaction products can be described by the general formula $[NP—(X—Y—Z)_2]_n$. If the Z groups are blocked by protective groups, these are changed into the reactive form according to conventional processes.

Tetrahydrofuran, toluene, dimethylsulfoxide, dimethylformamide, chloroform, methylene chloride, or pyridine, for example, can be used as inert solvents in which the reaction is carried out. Expedient reaction temperature is between 15 and 110° C., lower temperatures requiring longer reaction times.

Several examples of the phosphazene derivatives suitable according to the invention are shown in the following structural formulas.

The invention will be further explained by means of the following examples.

EXAMPLE 1

Phosphazene with functional hydroxy groups:

a) 2,2,4,4,6,6-hexakis-(4-hydroxyphenoxy)-cyclotriphosphazatriene $[NP(OC_6H_4OH)_2]_3$

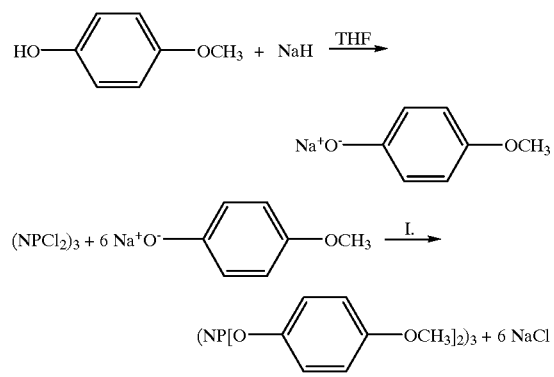

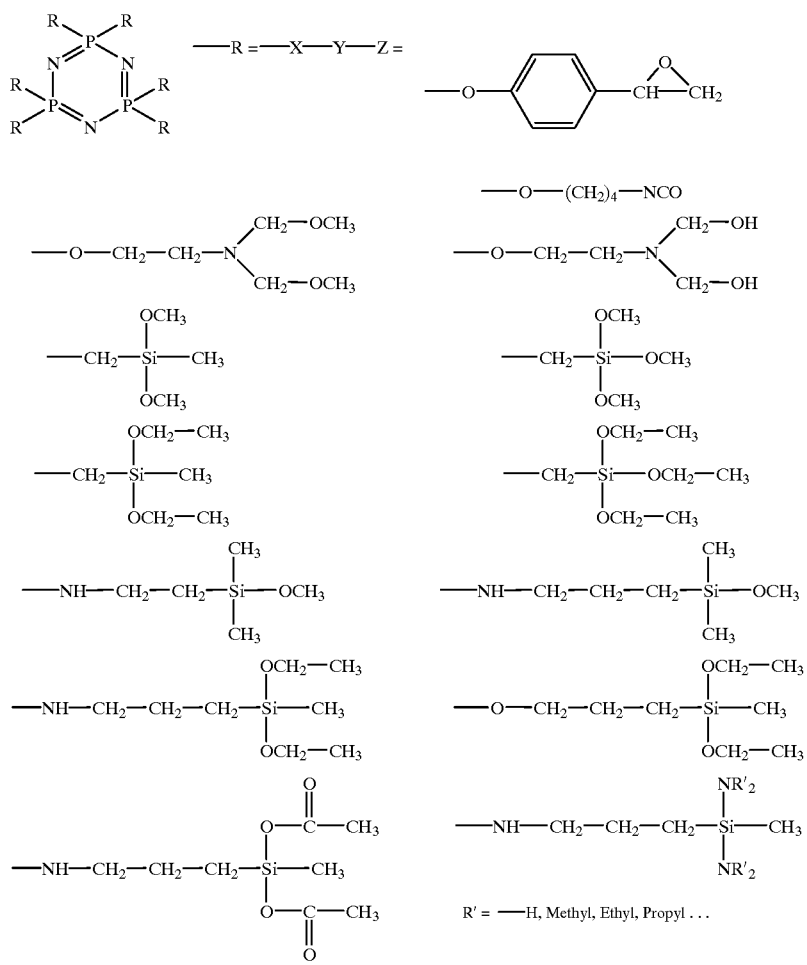

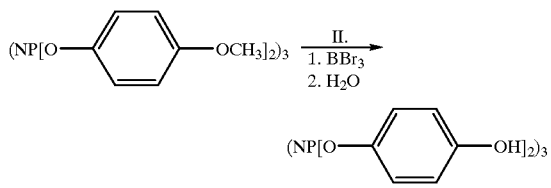

Reaction I is described in B. W. Fitzsimmons, R. A. Shaw, *J. Chem. Soc.*, London, Pages 1735–1741, 1964, and reaction II is described in A. Medici, G. Fantin, P. Pedrini, M. Gleria, F. Minto, *Macromolecules* 25, No. 10, Pages 2569–2574, 1992. An alternative synthesis path for the hydroquinone hydroxy group by means of a protective benzyl group is also disclosed in the latter literature document for reaction II.

b) 2,2,4,4,6,6-hexakis-(4-hydroxymethylphenoxy)-cyclotriphosphazatriene $[NP(OC_6H_4CH_2OH]_2]_3$

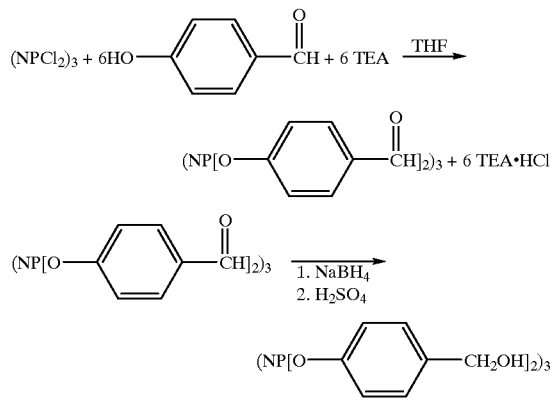

The reactions are described in M. Gleria, S. Lora, F. Minto, L. Busulini, P. Paolucci, *La Chimica et l'Industria*, Volume 63, No. 11, Pages 719–722, November 1981. As an alternative, the reaction can be carried out in a one-step synthesis using the phase transfer catalyst tetrabutylammonium bromide on the following synthesis path:

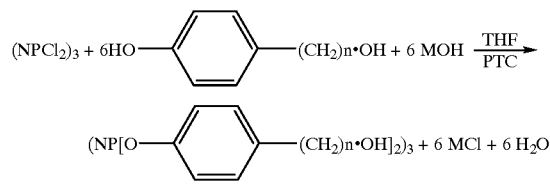

PTC=Phase Transfer Catalyst Tetrabutylammonium Bromide c) 2,2,4,4,6,6-hexakis-(hydroxyalkyloxy)-cyclotriphosphazatriene $[NP(O(CH_2)_nOH]_2]_3$

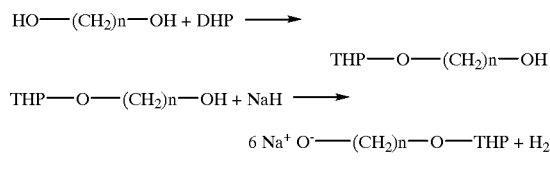

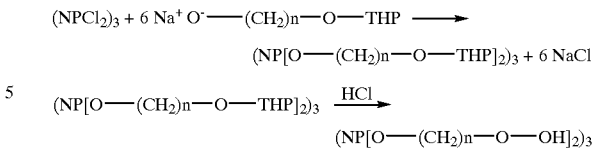

DHP=3,4-dihydro-2H-pyrane

The reactions are described in H. R. Allcock, C. G. Cameron, *Macromolecules* 27, Pages 3125–3130, 1994.

EXAMPLE 2

Phosphazene with functional epoxy groups:

a) 2,2,4,4,6,6-hexakis-(4-epoxymethoxyphenoxy)-cyclotriphosphazatriene $[NP(OC_6H_4OC_3H_5O]_2]_3$

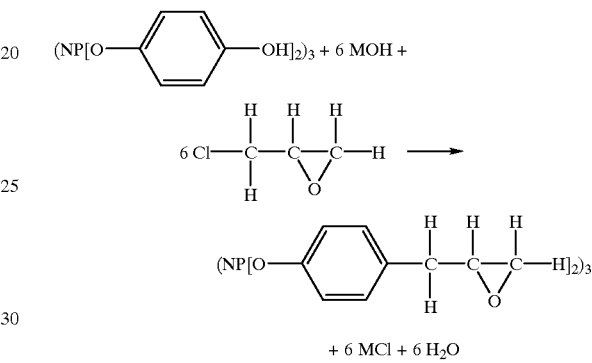

The reaction is described in G. Fantin, A. Medici, M. Fogagnolo, P. Petrini, M. Gleria, R. Bertani, G. Facchin, *Europ. Polym. J.*, Volume 29, No. 12, Pages 1571–1579, 1993. In the same literature document, another synthesis path for the above-mentioned phosphazene is described according to the following diagram:

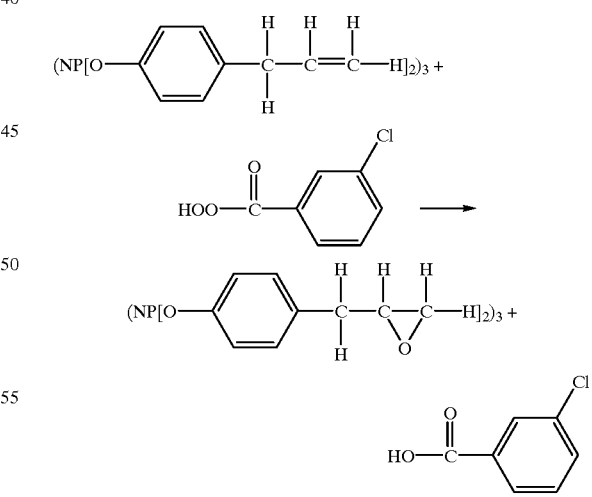

b) 2,2,4,4,6,6-hexakis-(4-undecanoyloxyphenoxyoxide)-cyclotriphosphazatriene $[NP(OC_6H_4OC(O)(CH_2)_7C_3H_5O]_2]_3$ The synthesis of this compound is also described in G. Fantin, A. Medici, M. Fogagnolo, P. Petrini, M. Gleria, R. Bertani, G. Facchin. *Europ. Polym. J.*, Volume 29, No. 12, Pages 1571–1579, 1993.

EXAMPLE 3

Phosphazene with functional amino groups:

a) 2,2,4,4,6,6-hexakis-(4-aminophenoxy)-cyclotriphosphazatriene [NP(OC$_6$H$_4$NH$_2$)$_2$]$_3$

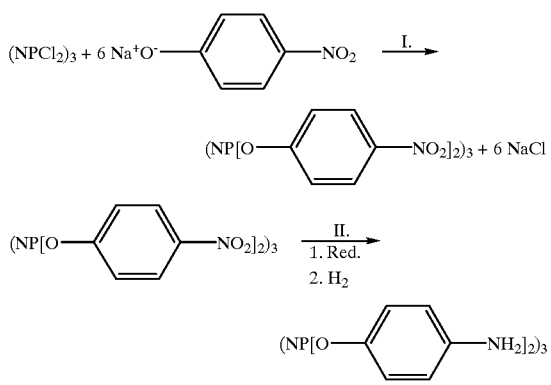

Reaction VII is described in E. Kober, H. Lederle, G. Ottmann, *Inorg. Chem.* 5, Pages 2239, 1966, and reaction VIII is described in G. Ottmann, H. Lederle, H. Hooks, Jr., E. Kober, *Inorg. Chem.* 6, Page 293, 1967.

b) By means of analogous reactions, 2,2,4,4,6,6-hexakis-[(4-aminophenyl)-alkylaminol]-cyclotriphosphazatriene compounds of the formula [NP(NH(CH$_2$)$_n$C$_6$H$_4$NH$_2$)$_2$]$_3$ can be synthesized, n being an integer from 1 to 10.

EXAMPLE 4

Phosphazene with functional isocyanate groups:

2,2,4,4,6,6-hexakis-(4-isocyanatophenoxy)-cyclotriphosphazatriene [NP(OC$_6$H$_4$NCO)$_2$]$_3$

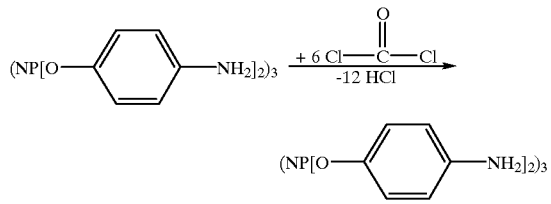

The reaction is described in G. Ottmann, H. Lederle, H. Hooks Jr., E. Kober, *Inorg. Chem.* 6, Page 394, 1967.

EXAMPLE 5

Phosphazene with functional carboxylic acid groups:

a) 2,2,4,4,6,6-hexakis-(4-carboxyphenoxy)-cyclotriphosphazatriene [NP(OC$_6$H$_4$COOH)$_2$]$_3$

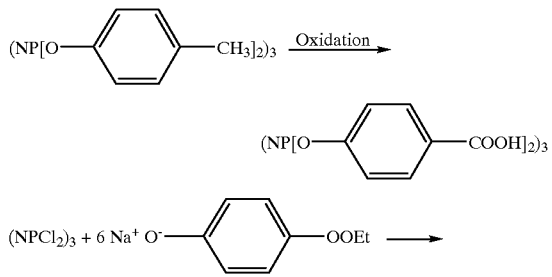

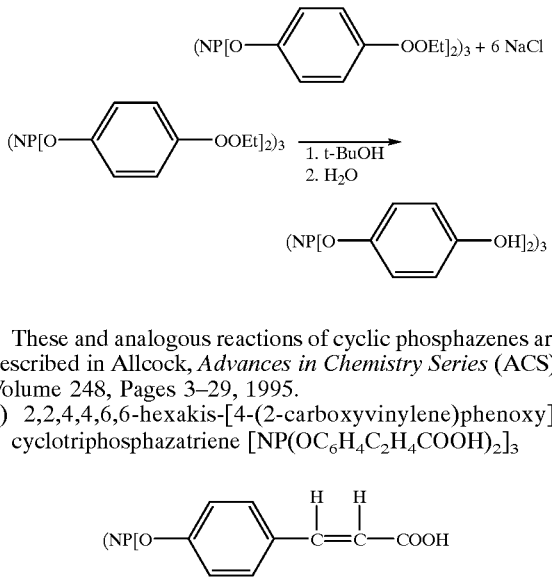

These and analogous reactions of cyclic phosphazenes are described in Allcock, *Advances in Chemistry Series* (ACS), Volume 248, Pages 3–29, 1995.

b) 2,2,4,4,6,6-hexakis-[4-(2-carboxyvinylene)phenoxy]-cyclotriphosphazatriene [NP(OC$_6$H$_4$C$_2$H$_4$COOH)$_2$]$_3$ (NP[O—⟨C$_6$H$_4$⟩—C(H)=C(H)—COOH The synthesis of this compound is described in M. Gleria, S. Lora, F. Minto, L. Busulini, P. Paolucci, *La Chimica et l'Industria*, Volume 63, No. 11, Pages 719–722, November 1981.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A hardenable composition comprising, in the non-hardened condition, at least one phosphazene derivative of the formula [NP—(X—Y—Z)$_2$]$_n$, wherein each X is the same or different radical from the group —O—, —S—, —NH— or —NR— (where R=C$_1$–C$_6$-alkyl);

each Y is the same or different aliphatic, cycloaliphatic, aromatic and/or heteroaromatic hydrocarbon groups which may optionally contain O, S and/or N;

each Z is the same or different functional radical from the group —OH, —NH$_2$, —NCO, —COOH, —CHO, N-methylol, acrylate, methacrylate, silyl, glycidyl or epoxy or precursor of the radicals from this group or radicals from this group which are blocked by protective groups, in which case no more than four Z radicals may also be —H; and n is an integer of at least 3 and no more than 10;

and at least one cross-linking agent, where the cross-linking agent has at least two functional groups selected from the Z radicals, which functional groups can react with the functional Z radicals of the phosphazene derivative.

2. A composition according to claim 1, wherein the NP radicals of the above formula are combined to a phosphazene ring and n is 3 or 4.

3. A composition according to claim 1, wherein X is oxygen.

4. A composition according to claim 3, wherein X is oxygen.

5. A composition according to claim 1, wherein the Y radical is linear or branched C$_1$–C$_{10}$-alkylene, C$_1$–C$_{10}$-oxyalkylene, C$_1$–C$_{10}$-alkylene phenyl, C$_1$–C$_{10}$-alkylene carboxyphenyl, phenylene, biphenylene, alkaoxyphenylene or oxyphenylene.

6. A composition according to claim 2, wherein the Y radical is linear or branched $C_1$–$C_{10}$-alkylene, $C_1$–$C_{10}$-oxyalkylene, $C_1$–$C_{10}$-alkylene phenyl, $C_1$–$C_{10}$-alkylene carboxyphenyl, phenylene, biphenylene, alkaoxyphenylene or oxyphenylene.

7. A composition according to claim 3, wherein the Y radical is linear or branched $C_1$–$C_{10}$-alkylene, $C_1$–$C_{10}$-oxyalkylene, $C_1$–$C_{10}$-alkylene phenyl, $C_1$–$C_{10}$-alkylene carboxyphenyl, phenylene, biphenylene, alkaoxyphenylene or oxyphenylene.

8. A composition according to claim 4, wherein the Y radical is linear or branched $C_1$–$C_{10}$-alkylene, $C_1$–$C_{10}$-oxyalkylene, $C_1$–$C_{10}$-alkylene phenyl, $C_1$–$C_{10}$-alkylene carboxyphenyl, phenylene, biphenylene, alkaoxyphenylene or oxyphenylene.

9. A composition according to claim 1, wherein the Y radical is

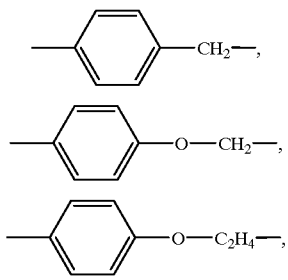

1,4-phenylene, $C_1$–$C_{10}$-alkylphenylene or $C_1$–$C_{10}$-alkylcarboxylphenylene.

10. A composition according to claim 2, wherein the Y radical is

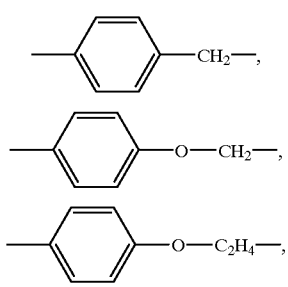

1,4-phenylene, $C_1$–$C_{10}$-alkylphenylene or $C_1$–$C_{10}$-alkylcarboxylphenylene.

11. A composition according to claim 3, wherein the Y radical is

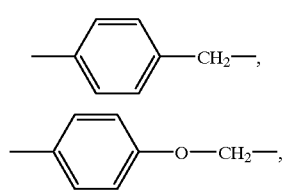
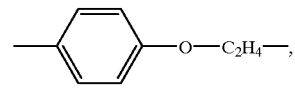

1,4-phenylene, $C_1$–$C_{10}$-alkylphenylene or $C_1$–$C_{10}$-alkylcarboxylphenylene.

12. A composition according to claim 4, wherein the Y radical is

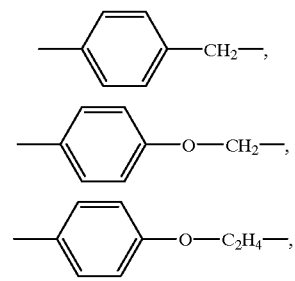

1,4-phenylene, $C_1$–$C_{10}$-alkylphenylene or $C_1$–$C_{10}$-alkylcarboxylphenylene.

13. A composition according to claim 5, wherein the Y radical is

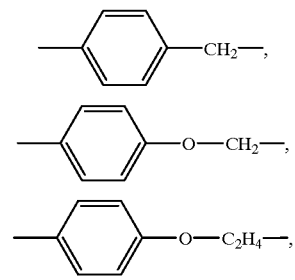

1,4-phenylene, $C_1$–$C_{10}$-alkylphenylene or $C_1$–$C_{10}$-alkylcarboxylphenylene.

14. A composition according to claim 6, wherein the Y radical is

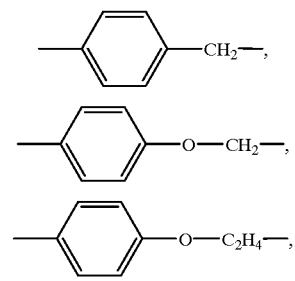

1,4-phenylene, $C_1$–$C_{10}$-alkylphenylene or $C_1$–$C_{10}$-alkylcarboxylphenylene.

15. A composition according to claim 7, wherein the Y radical is

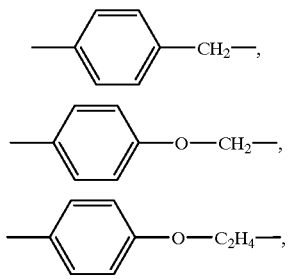

1,4-phenylene, $C_1$–$C_{10}$-alkylphenylene or $C_1$–$C_{10}$-alkylcarboxylphenylene.

16. A composition according to claim 8, wherein the Y radical is

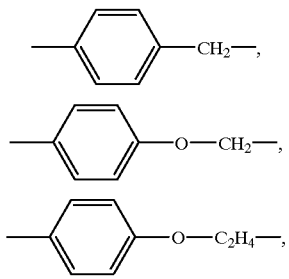

1,4-phenylene, $C_1$–$C_{10}$-alkylphenylene or $C_1$–$C_{10}$-alkylcarboxylphenylene.

17. A composition according to claim 1, wherein n is equal to 3, and wherein 2, 3, or 4 of the Z radicals are acrylate or methacrylate radicals.

18. A composition according to claim 2, wherein n is equal to 3, and wherein 2, 3, or 4 of the Z radicals are acrylate or methacrylate radicals.

19. A composition according to claim 3, wherein n is equal to 3, and wherein 2, 3, or 4 of the Z radicals are acrylate or methacrylate radicals.

20. A composition according to claim 4, wherein n is equal to 3, and wherein 2, 3, or 4 of the Z radicals are acrylate or methacrylate radicals.

21. A composition according to claim 5, wherein n is equal to 3, and wherein 2, 3, or 4 of the Z radicals are acrylate or methacrylate radicals.

22. A composition according to claim 6, wherein n is equal to 3, and wherein 2, 3, or 4 of the Z radicals are acrylate or methacrylate radicals.

23. A composition according to claim 7, wherein n is equal to 3, and wherein 2, 3, or 4 of the Z radicals are acrylate or methacrylate radicals.

24. A composition according to claim 8, wherein n is equal to 3, and wherein 2, 3, or 4 of the Z radicals are acrylate or methacrylate radicals.

25. A composition according to claim 9, wherein n is equal to 3, and wherein 2, 3, or 4 of the Z radicals are acrylate or methacrylate radicals.

26. A composition according to claim 10, wherein n is equal to 3, and wherein 2, 3, or 4 of the Z radicals are acrylate or methacrylate radicals.

27. A composition according to claim 11, wherein n is equal to 3, and wherein 2, 3, or 4 of the Z radicals are acrylate or methacrylate radicals.

28. A composition according to claim 12, wherein n is equal to 3, and wherein 2, 3, or 4 of the Z radicals are acrylate or methacrylate radicals.

29. A composition according to claim 13, wherein n is equal to 3, and wherein 2, 3, or 4 of the Z radicals are acrylate or methacrylate radicals.

30. A composition according to claim 14, wherein n is equal to 3, and wherein 2, 3, or 4 of the Z radicals are acrylate or methacrylate radicals.

31. A composition according to claim 15, wherein n is equal to 3, and wherein 2, 3, or 4 of the Z radicals are acrylate or methacrylate radicals.

32. A composition according to claim 16, wherein n is equal to 3, and wherein 2, 3, or 4 of the Z radicals are acrylate or methacrylate radicals.

33. A method for producing a hardenable composition for lacquers, coating agents, fillers, knifing fillers, adhesives, preforms or foils, comprising using a phosphazene derivative of the formula $[NP-(X-Y-Z)_2]_n$, wherein:

- each X is the same or different radical from the group —O—, —S—, —NH— or —NR— (R=$C_1$–$C_6$-alkyl);
- each Y is the same or different aliphatic, cycloaliphatic, aromatic and/or heteroaromatic hydrocarbon groups which may optionally contain O, S and/or N;
- each Z is the same or different functional radical from the group —OH, —$NH_2$, —NCO, —COOH, —CHO, —CH=$CH_2$, allyl, N-methylol, acrylate, methacrylate, silyl, glycidyl or epoxy or precursor of the radicals from this group or radicals from this group which are blocked by protective groups, in which case no more than four Z radicals may also be —H; and
- n is an integer of at least 3 and no more than 10.

34. A method according to claim 33, further comprising using at least one cross-linking agent with at least two functional groups which can react with the functional Z radicals of the phosphazene derivative.

* * * * *